United States Patent [19]

Kwantes et al.

[11] 4,395,576

[45] Jul. 26, 1983

[54] PROCESS FOR THE PREPARATION OF ETHANOL

[75] Inventors: Arien Kwantes, Amsterdam; Cornelis W. J. De Goederen, The Hague, both of Netherlands

[73] Assignee: Shell Oil Company, Houston, Tex.

[21] Appl. No.: 272,617

[22] Filed: Jun. 11, 1981

[30] Foreign Application Priority Data

Jun. 12, 1980 [NL] Netherlands ............ 8003405

[51] Int. Cl.$^3$ ............ C07C 29/04; C07C 29/80
[52] U.S. Cl. ............ 568/913; 203/32; 568/895; 568/914
[58] Field of Search ............ 568/913, 895, 899, 914; 203/32

[56] References Cited

U.S. PATENT DOCUMENTS

| | | | |
|---|---|---|---|
| 2,744,939 | 5/1956 | Kennel | 203/32 X |
| 2,770,636 | 11/1956 | Steitz | 203/32 X |
| 2,944,087 | 7/1960 | Nommensen et al. | 568/914 |
| 3,678,118 | 7/1972 | Frampton et al. | 568/914 X |
| 3,960,672 | 6/1976 | Ester et al. | 203/37 |
| 3,990,952 | 11/1976 | Katzen et al. | 203/37 X |

FOREIGN PATENT DOCUMENTS 1903552  6/1976  Fed. Rep. of Germany.

OTHER PUBLICATIONS

Johnson et al., Chemistry & Industry, (Aug. 1953), pp. 528-531.

*Primary Examiner*—Bernard Helfin
*Attorney, Agent, or Firm*—Ronald R. Reper; Ronald L. Clendenen

[57] ABSTRACT

A process for the preparation of ethanol by catalytic hydration of ethylene in which the crude ethanol is separated by distillation in a first column into a bottom stream consisting of aqueous ethanol and a top stream containing diethyl ether and acetaldehyde, the bottom stream is processed further in a second column, the top stream is hydrogenated and then fractionated in a third column together with an impurities containing stream originating from the second column, and optionally the diethyl ether containing top stream of the third column is recycled to the hydration reactor.

12 Claims, 1 Drawing Figure

PROCESS FOR THE PREPARATION OF ETHANOL

BACKGROUND OF THE INVENTION

1. Field of the Invention

The invention relates to a process for the preparation of ethanol.

2. Background

The preparation of ethanol by catalytic hydration of ethylene is known, for example, from Hydrocarbon Processing & Petroleum Refiner, November 1963, Volume 42, No. 11, page 162. In the method described in said article a liquid condensate is obtained by cooling down the effluent gas mixture from the reactor. After having been scrubbed with water the noncondensed gases are recycled to the reactor and the condensate and scrubbing liquid are combined. The resultant mixture consists of an aqueous solution of ethanol containing diethyl ether and acetaldehyde as principal impurities. The ethanol is steam-stripped from the aqueous solution, together with the impurities. The impure alcohol is passed over a nickel catalyst with hydrogen, in which treatment, inter alia, the acetaldehyde is converted into ethanol. Subsequently, in the purification section of the plant the low-boiling by-products, mainly diethyl ether, are removed overhead from a distillation column and a mixture of ethanol and water of substantially aceotropic composition is obtained by fractional distillation of the bottom product in a second distillation column.

In an article by T. C. Carle and D. M. Stewart in Chemistry and Industry, 12th May, 1962, pages 830–839, various by-products are enumerated that can be formed in the hydration of ethylene. From the above-mentioned acetaldehyde, crotonaldehyde can be formed under certain conditions by aldol condensation followed by dehydration. Further, higher olefins with up to 8 carbon atoms, in particular butylene, are formed by polymerization of ethylene. Higher alcohols can be formed from said olefins by reaction with water. One of said alcohols is butanol-2, which can be dehydrogenated into methyl ethyl ketone in the reactor.

It is not simple to prepare pure ethanol from crude alcohol in an economically justified manner. In the methods described in the above-mentioned articles the crude ethanol is catalytically hydrogenated. In this treatment the aldehydes and ketones are converted into the corresponding alcohols. The higher alcohols can be separated from ethanol more readily than the aldehydes. These methods still have the disadvantage that the hydrogenation of large quantities of crude ethanol is less attractive for technical and economic reasons and, therefore, other methods have been developed.

In German patent application DAS No. 1 903 552 a purified mixture of ethanol and water of about azeotropic composition is obtained from the crude aqueous ethanol by distillation in three columns. In said process the aqueous crude ethanol containing both lower-boiling and higher-boiling impurities is distilled extractively in a first distillation column, water being added at the top of the column. In this column the greater part of the impurities, both the higher- and the lower-boiling impurities, distills overhead. As bottom product aqueous ethanol with a concentration of about 5-10% is obtained which is purified and concentrated in a second distillation column. The purified ethanol-water azeotrope is obtained as a side stream from the upper part of the second column. The lower-boiling impurities distill overhead from said column and the higher-boiling impurities leave the column as one or more side streams. The top products of the first and second column and the impurities-containing side stream or side streams of the second column are introduced into a third distillation column. From the upper part of the third column an ethanol-rich side stream is obtained that is recycled to the first column. Higher-boiling impurities are discharged as one or more side streams and lower-boiling impurities, such as diethyl ether and acetaldehyde, are removed from the system via the top of the third column. It appears from German patent application DAS No. 1 903 552 that the diethyl ether and acetaldehyde-containing top stream of the third column still mainly consists of ethanol. This loss of ethanol, however, is considered as inevitable. Further, the method of German patent application DAS No. 1 903 552 has the disadvantage that aldehydes, such as acetaldehyde and crotonaldehyde are ultimately present throughout the purification section of the plant. This has an unfavourable effect on the quality of the ethanol.

German patent application DAS No. 2 106 073 (U.S. equivalent being U.S. Pat No. 3,960,672 issued June 1, 1976) recommends that aqueous caustic lye be added to the second distillation column of the above-mentioned process below the point where ethanol is collected but above the point where the higher-boiling impurities leave the column, and that the bottom product of the second column, after neutralization, be discharged or introduced into the upper part of the first column. This results in the recovery of ethanol of better quality with mainly a lower acetaldehyde content and a better permanganate time. However, this method has the disadvantage that in the system a gradual increase takes place of inorganic and organic impurities (polymers) causing corrosion and pollution. Further, accurate neutralization of the caustic lye requires the use of rather complicated apparatus. Further, this process has also the disadvantage that the top stream to be removed from the third distillation column contains considerable quantities of ethanol, diethyl ether and acetaldehyde. It appears from Examples 2 and 3 of German patent application DAS No. 2 106 073 that the ethanol can be recovered by means of extractive distillation with water in a fourth distillation column and recycled to the first distillation column. However, the process is cumbersome and not very economic and, moreover, the resultant aqueous ethanol will again contain acetaldehyde owing to the high solubility of acetaldehyde in water. With regard to the ether recovered in the extractive distillation, said patent application only mentions that it can serve as raw material for producing ether. Consequently, the ether is apparently still highly contaminated. In this connection it is noted that the distillative separation of diethyl ether and acetaldehyde is greatly impeded by azeotrope formation.

German patent application DAS 2 545 508 (equivalent to U.S. Pat. No. 3,990,950 issued Nov. 9, 1976) also states that the process according to German patent application DAS No. 2 106 073 has the disadvantage of excessive use of lye and neutralizing acid. Even if the aqueous bottom product of the second column is not recycled to the first column, the alkali present should be neutralized before the bottom stream can be discharged, in order to prevent environmental pollution. However, drawbacks are also involved in the discharge of water containing large quantities of salts. Therefore, in the published German patent application DAS No. 2 545 508 the quantity of caustic lye that is added to the second column is kept within specified low limits. Consequently, ethanol with a lower acetaldehyde content is obtained, but it is obvious that the above-mentioned drawbacks were not eliminated

SUMMARY OF THE INVENTION

The invention relates to a process for preparing ethanol by catalytic hydration of ethylene in a reaction section, in which process aqueous crude ethanol containing both higher- and lower-boiling impurities is obtained by condensing and scrubbing the gaseous reaction mixture and in a purification section the aqueous crude ethanol is passed into a first distillation column, a top fraction containing the greater portion of the impurities is discharged from said column, the bottom product of the first distillation column is passed to a second distillation column, ethanol-water azeotrope is recovered as a side stream from the upper part of the second distillation column, one or more side streams containing higher-boiling impurities are passed from a lower part of the second distillation column to a third distillation column, a top fraction containing lower-boiling impurities is removed from the third column, an ethanol-containing side stream is discharged from the upper part of the third column and one or more side streams containing higher-boiling impurities are removed from a lower part, characterized in that the top fraction of the first distillation column is wholly or partly hydrogenated and the hydrogenated product is fractionated in the third distillation column.

DESCRIPTION OF THE PREFERRED EMBODIMENT

Figure 1:
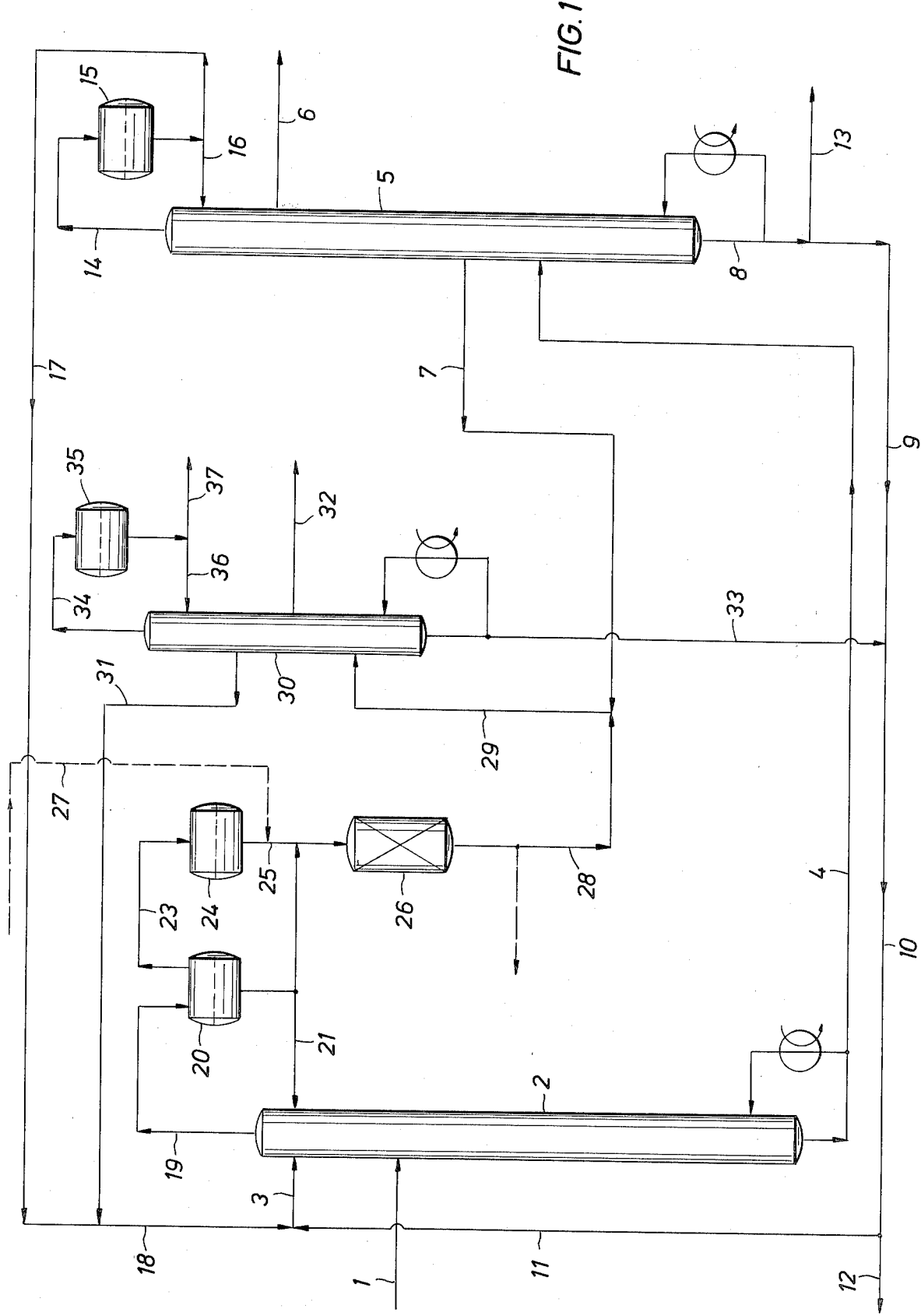
FIG. 1 is a diagrammatic flow sheet of a preferred embodiment of the process of the invention.

The invention relates to a process for preparing ethanol by catalytic hydration of ethylene in a reaction section, in which process aqueous crude ethanol containing both higher- and lower-boiling impurities is obtained by condensing and scrubbing the gaseous reaction mixture and in a purification section the aqueous crude ethanol is passed into a first distillation column, a top fraction containing the greater portion of the impurities is discharged from said column, the bottom product of the first distillation column is passed to a second distillation column, ethanol-water azeotrope is recovered as a side stream from the upper part of the second distillation column, one or more side streams containing higher-boiling impurities are passed from a lower part of the second distillation column to a third distillation column, a top fraction containing lower-boiling impurities is removed from the third column, an ethanol-containing side stream is discharged from the upper part of the third column and one or more side streams containing higher-boiling impurities are removed from a lower part, characterized in that the top fraction of the first distillation column is wholly or partly hydrogenated and the hydrogenated product is fractionated in the third distillation column.

The top fraction of the third distillation column containing the greater part of the diethyl ether formed as by-product is preferably wholly or partly recycled to the reaction section. The above-mentioned article by Carle and Stewart explains that the formation of diethyl ether from ethanol is an equilibrium reaction, so that by recycling of diethyl ether to the reactor the conversion of ethanol into diethyl ether is limited and the yield of ethanol is increased. In the processes according to German patent applications DAS No. 1 903 552, 2 106 073 and No. 2 545 508 such a recycling of the top stream from the third distillation column is impossible in particular owing to the acetaldehyde present therein, since this would result in a continuous increase in the aldehyde content of the various liquid streams. Owing to the hydrogenation of the top fraction of the first distillation column applied according to the invention, the top fraction of the third column contains virtually no acetaldehyde and there is no danger that the concentration of said compound or of other compounds formed therefrom in the system will be increased by recycling.

The fractionation in the third column is preferably so carried out that the top fraction consists mainly, for example more than 80% by weight thereof, of diethyl ether. The process according to the invention therefore has the advantage that the yield of ethanol is improved both by the conversion of acetaldehyde into ethanol and by the fact that it is now possible to recycle diethyl ether to the reaction section. Moveover, the process is very simple; use of a fourth distillation column, as in German patent aplication DAS No. 2 106 073, is superfluous. Further, according to the invention very pure ethanol can be prepared without caustic lye having to be added to the second distillation column, although the possibility of such an addition is not excluded. The aqueous bottom product of the second distillation column can therefore without objection be discharged and/or used as extraction liquid in the extractive distillation optionally applied in the first distillation column and/or be used as scrubbing liquid in the reaction section of the plant. Since the aqueous bottom product is still hot, its recycling can have an energy-saving effect.

The purification of diethyl ether obtained as by-product in the preparation of ethanol by catalytic hydration of ethylene by means of hydrogenation, preferably in the gas phase, is known from the published Japanese patent application No. 32,763-1979. Said patent specification, however, is exclusively directed to the preparation of very pure diethyl ether, for example for pharmaceutical purposes; the problems associated with the preparation of pure ethanol from crude ethanol are not discussed. It is impossible to derive from said patent specification that by hydrogenation of the top stream of the first distillation column and subsequently passing it to a distillation column where non-hydrogenated higher-boiling impurities are also introduced, the above-mentioned drawbacks of the processes of the German patent specifications No. 1 903 552, 2 106 073 and 2 545 508, such as the necessary addition of caustic lye to the second column, can be eliminated and ethanol of a very high quality can be obtained. it is also pointed out in the Japanese patent application that the problems involved in the preparation of pure ethanol or pure diethyl ether differ widely from each other. It is surprising that ethanol of very high quality can be obtained by means of the process according to the invention in which only the top fraction of the first distillation column is hydrogenated and the greater portion of the ethanol contaminated with higher-boiling compounds leaves said column as bottom stream without lye being added somewhere in the purification section.

The first distillation column is preferably an extractive distillation column, water being introduced into the upper part of the column. The quantity of water and the supply of heat to the bottom part of the column must be sufficient to ensure that the greater portion of the impurities leave the column overhead. However, the first distillation column can also be an ordinary fractionation column. The fact that the crude alcohol generally has a high water content can help to cause higher-boiling impurities together with the lower-boiling impurities which as such already constitute the greater part of the impurities, to leave the column as top fraction, even without water being supplied from outside. Higher-boiling impurities that have remained behind in the aqueous alcohol leaving the first distillation column as bottom stream are removed from the system via the second and third column. In the first distillation column both atmospheric pressure and gauge pressure, for example a pressure between 3 and 10 bar abs., can be used. The use of guage pressure has the advantage that both the top stream and the bottom stream of said column have an elevated temperature. The heat present in the relevant streams can be used by means of heat exchangers for heating up for example the second distillation column, which has an energy-saving effect.

The top fraction of the first distillation column can be hydrogenated in the gaseous or liquid state or partly in the gaseous and partly in the liquid state. Hydrogenation in the liquid state is preferred. Hydrogenation is preferably carried out in the presence of a hydrogenation catalyst. The top fraction of the first distillation column can be cooled by means of one or more heat exchangers and the condensate can be separated off. This condensate, part of which can, if desired, be recycled to the top of the first distillation column, is passed together with hydrogen to the hydrogenation reactor containing a hydrogenation catalyst. The condensate may optionally consist of two immiscible liquid phases, an ethereal and an aqueous phase.

Hydrogenation is carried out in such a manner that the aldehydes and ketones present in the top fraction are at least largely converted into the corresponding alcohols. Any catalyst suitable for the hydrogenation of aldehydes and ketones can be used, in particular nickel catalysts, for example Raney nickel or catalysts consisting of nickel on a carrier. Suitable carriers are, for example, diatomaceous earth, silica gel, alumina, pumice and activated carbon. Platinum-containing catalysts can also be used. Hydrogenation can be carried out at atmospheric or elevated pressure. Use of gauge pressure is preferred; pressures between 10 and 50 bar abs., in particular between 15 and 25 bar abs., are very suitable. Hydrogenation is preferably carried out at a temperature between 60° and 140° C., in particular between 80° and 120° C. The quantity of hydrogen is preferably 1–3, in particular 1.5–2 moles per mole of carbonyl compound present as impurity. The space velocity preferably lies between 1 and 8 liters of the liquid hydrogenation mixture per liter of catalyst per hour.

The bottom stream of the first column consisting of aqueous ethanol is fractionated in the second distillation column. A pure, substantially azeotropic mixture of ethanol and water is recovered as a side stream. The top stream of the second distillation column is partly recycled as reflux to said column. The remaining part of the top stream can be passed to the first distillation column and, if desired, be introduced there at a higher point than the crude aqueous ethanol feed; when an extractive distillation column is used, the remaining part can for example be introduced at the same height as the extraction water. At a lower point than where the ethanol product is recovered from the second column, for example above the point where the aqueous bottom stream of the first column is introduced, one or more side streams containing higher-boiling impurities, such as butanols, is/are discharged from the second distillation column and passed to the third distillation column. The bottom stream of the second column practically consisting of pure water can in the event of the first column being an extractive distillation column be recycled as extraction water to said column and/or be discharged. The distillation in the second column can very suitably be carried out at atmospheric pressure. If desired, a light vacuum can also be used to increase the ethanol concentration of the product.

The hydrogenated top fraction of the first column can be introduced into the third column after the excess hydrogen has been separated off, very suitably after combination with the higher-boiling impurities-containing side stream or side streams of the second column. As already stated, the top stream of the third column, for the greater part consisting of diethyl ether, is preferably wholly or partly recycled to the reaction section. Part of the top stream can be recycled as reflux to the third column. The fractionation in the third column is preferably so carried out that the ethanol-containing side stream discharged from the upper part of the third column does not contain more than 5% by weight of impurities. The above side stream is preferably passed to the first column and introduced there preferably at a higher point than the crude aqueous ethanol, for example together with the recycled top fraction of the second column. In this manner it is ensured that impurities present in said recycle stream remain in the top of the first column and cannot find their way to the alcohol-containing bottom stream of the first column. Further, the fractionation in the third column is preferably so carried out that the higher-boiling impurities-containing side stream or side streams, discharged from a lower part of the third column, contains/contain the greatest part, preferably more than 90% by weight, of the higher-boiling impurities. If desired, the ethanol still present in said stream can be recovered by extraction with water and be recycled to the feed line of the third column. In contrast to the known methods, and apart from the diethyl ether, substantially no impurities are present in the top stream of the third column. The fractionation in the third column is preferably carried out at atmospheric pressure or a low gauge pressure, for example a pressure of up to 2 bar abs.

EXAMPLE

In this Example the various streams are designated with the reference numerals used in FIG. 1.

Crude aqueous ethanol obtained by catalytic hydration of ethylene and containing 14.35% by weight of ethanol, 85.16% by weight of water, 0.42% by weight of diethyl ether, 0.04% by weight of acetaldehyde and 0.03% by weight of higher alcohols, ketones and polymers, was introduced into the upper half of the extractive distillation column 2 through line 1 at a rate of 40.4 kg/h. The pressure in the column was 3.5 bar abs. and the top and bottom temperatures were 114° and 128° C. respectively. A stream containing 98% by weight of water and for the greater part consisting of the recycled aqueous bottom stream of column 5 was introduced at the top of the column via line 3. The top stream was passed via line 19 to cooler 20 where a mixture of two liquid phases was separated off. Part thereof was recycled as reflux to column 2 via line 21 and the ohter part was passed to the hydrogenation reactor 26 via line 25. The gaseous phase was passed to cooler 24 via line 23 and the condensate formed there was passed to the hydrogenation reactor via line 25. Hydrogen was injected into the line 25 via line 27. The molar ratio between the added quantity of hydrogen and the quantity of carbonyl compounds present in the liquid was 2:1. The mixture of the two liquid phases and the hydrogen was passed through the hydrogenation reactor at a space velocity of 1.8 liter of liquid per liter of catalyst per hour. The catalyst consisted of nickel on alumina and had a nickel content of 65% by weight. the specific surface area of the catalyst was 158 m$^2$/g and the pore volume was 0.36 ml/g. Hydrogenation was carried out at a total pressure of 20 bar abs. and a temperature of 120° C. After the excess hydrogen had been separated off the hydrogenated product was introduced into the lower half of distillation column 30 through lines 28 and 29. The bottom product of column 2 containing 9.98% by weight of ethanol, 90.01% by weight of water and 0.01% by weight of higher alcohols, ketones and polymers, was introduced into the lower half of the distillation column 5 via line 4. The pressure in said column was atmospheric and the top and bottom temperatures were 85° C. and 109° C. respectively. Five trays below the top a pure mixture of ethanol and water of substantially azeotropic composition containing 93.82% by weight of ethanol and 6.18% by weight of water and no measurable quantities of acetaldehyde was discharged from column 5 via line 6. An aqueous stream containing higher-boiling impurities was removed from column 5 at the 7th, 10th and 13th tray from the bottom via a line 7 and added to the stream of line 28. The pressure in column 30 was 1.5 bar abs. and the top and bottom temperatures were 49° and 120° C. respectively. All impurities to be discharged from the system were removed from column 30 from 2 trays located just above the feed tray via line 32. The flow in line 32 was 145 g per hour and consisted of 72.31% by weight of ethanol, 18.67% by weight of water, 1.29% by weight of diethyl ether and 7.73% by weight of higher alcohols, ketones and polymers. The top stream of column 30 was passed to cooler 35 through line 34. The condensate consisting of 14.22% by weight of ethanol, 85.70% by weight of diethyl ether and 0.08% by weight of acetone was partly recycled to column 30 via line 36 and partly pumped back to the reaction section through line 37 at a rate of 195 g/h. Ten trays from the top, impure aqueous ethanol containing 78.84% by weight of ethanol, 17.97% by weight of water, 0.57% by weight of diethyl ether and 2.62% by weight of higher-boiling impurities was recycled to column 2 at a rate of 275 g/h through lines 31, 18 and 3 and introduced there on the top tray. The top stream of column 5 was passed to cooler 15 through line 14 and the condensate through line 16 was partly recycled to column 2 via lines 17, 18 and 3. The aqueous bottom stream of column 5 was largely recycled to the top of column 2 through lines 8, 9, 10, 11 and 3. A small portion was discharged from the system via line 13. The aqueous bottom stream of column 30 was recycled to column 2 through lines 33, 10, 11 and 3. A small portion of the aqueous stream in line 10, consisting of water for 99.5% by weight, the remainder being mainly ethanol, was passed to the reaction section via line 12.

We claim:

1. A process for the preparation of ethanol by catalytic hydration of ethylene in a reaction section, in which process aqueous crude ethanol containing both higher- and lower-boiling impurities is obtained by condensing and scrubbing the gaseous reaction mixture and in a purifying section the aqueous crude ethanol is passed into a first distillation column, a top fraction containing the greater portion of the impurities is discharged from said column, the bottom product of the first distillation column is passed to a second distillation column, ethanol-water azeotrope is recovered as a side stream from the upper part of the second distillation column, one or more side streams containing high-boiling impurities are passed from a lower part of the second distillation column to a third distillation column, a top fraction containing lower-boiling impurities is removed from the third column, an ethanol-containing side stream is discharged from the upper part of the third column and one or more side streams containing higher-boiling impurities are removed from a lower part, characterized in that the top fraction of the first distillation column is wholly or partly hydrogenated at a pressure between 10 and 50 bar abs. and a temperature between 60° C. and 140° C., the hydrogenated product is fractionated in the third distillation column, and that the top fraction obtained by fractionation in the third column is recycled completely or partly into the reaction section.

2. The process as claimed in claim 1, characterized in that the top fraction of the first distillation column or part thereof is hydrogenated in the liquid state in the presence of a hydrogenation catalyst.

3. The process as claimed in claim 1 characterized in that the pressure lies between 15 and 25 bar abs.

4. The process as claimed in claim 1 characterized in that the quantity of hydrogen is 1–3 moles per mole of carbonyl compound present as impurity.

5. The process as claimed in claim 1 characterized in that the hydrogenation is carried out at a space velocity between 1 and 8 liters of liquid hydrogenation mixture per liter of catalyst per hour.

6. The process as claimed in claim 1 characterized in that the top fraction obtained by fractionation in the third column consists of more than 80% by weight of diethyl ether.

7. The process as claimed in claim 1 characterized in that the fractionation in the third column is so carried out that the ethanol-containing side stream discharged from the upper part of the third column does not contain more than 5% by weight of impurities.

8. The process as claimed in claim 7, characterized in that the ethanol-containing side stream of the third column is passed to the first column and is introduced there at a higher point than the crude aqueous ethanol.

9. The process as claimed in claim 1 characterized in that the fractionation in the third column is so carried out that the higher-boiling impurities-containing side stream or side streams discharged from a lower part of the third column contain(s) more than 90% by weight of the higher-boiling impurities.

10. The process as claimed in claim 1 characterized in that the fractionation in the third column is carried out at atmospheric pressure or at a pressure up to 2 bar abs.

11. The process as claimed in claim 1 characterized in that the first distillation column is an extractive distillation column in which water is introduced into the upper part of the column.

12. The process as claimed in claim 1 characterized in that superatmospheric pressure is used in the first distillation column.

* * * * *